United States Patent [19]
Jackson et al.

[11] Patent Number: 5,670,702
[45] Date of Patent: Sep. 23, 1997

[54] LIQUID PHASE PREPARATION OF (METH)-ACRYLATE FROM ALPHA-OLEFIN

[75] Inventors: Barrie W. Jackson, Perth; Thomas J. Harris, Amherstview, both of Canada

[73] Assignee: Queen's University at Kingston, Kingston, Canada

[21] Appl. No.: 544,494

[22] Filed: Oct. 18, 1995

Related U.S. Application Data

[63] Continuation of Ser. No. 238,401, May 5, 1994, abandoned.

[51] Int. Cl.⁶ ................................................. C07C 67/00
[52] U.S. Cl. ................................................. 560/208
[58] Field of Search ..................................... 560/208

[56] References Cited

U.S. PATENT DOCUMENTS

| | | | |
|---|---|---|---|
| 3,621,054 | 11/1971 | Olivier | 260/533 |
| 3,625,995 | 12/1971 | Brattesani | 260/486 |
| 3,658,886 | 4/1972 | Sennewald et al. | 260/486 |
| 3,734,950 | 5/1973 | Scharfe et al. | 260/484 |
| 3,758,551 | 9/1973 | Murib et al. | 260/486 |
| 3,776,947 | 12/1973 | Shimizu et al. | 260/486 R |
| 3,925,463 | 12/1975 | Ferlazzo et al. | 260/486 |
| 3,927,111 | 12/1975 | Robinson | 260/604 |
| 4,055,721 | 10/1977 | Kawata et al. | 560/207 |
| 4,088,822 | 5/1978 | Ogawa et al. | 560/207 |
| 4,356,316 | 10/1982 | Aoshima et al. | 560/208 |
| 4,436,946 | 3/1984 | Smutny | 585/510 |
| 4,520,125 | 5/1985 | Baer et al. | 502/170 |
| 4,595,778 | 6/1986 | Duembgen et al. | 560/208 |
| 4,622,424 | 11/1986 | Callahan et al. | 562/545 |
| 4,647,706 | 3/1987 | Cheminal et al. | 568/842 |
| 4,781,868 | 11/1988 | Langerbeins | 260/549 |
| 4,816,603 | 3/1989 | Oh-Kita et al. | 562/538 |
| 4,874,890 | 10/1989 | Kato et al. | 560/205 |
| 4,954,650 | 9/1990 | Abe et al. | 562/534 |
| 4,956,493 | 9/1990 | Ueoka et al. | 560/208 |
| 5,009,872 | 4/1991 | Chuang et al. | 423/245.3 |
| 5,011,980 | 4/1991 | Sano et al. | 560/245 |
| 5,210,319 | 5/1993 | Chuang | 562/546 |
| 5,227,564 | 7/1993 | Chen et al. | 585/640 |

FOREIGN PATENT DOCUMENTS

| | | | |
|---|---|---|---|
| 1234797 | 4/1988 | Canada | 252/91 |
| 1238052 | 6/1988 | Canada | 260/520.5 |
| 1238053 | 6/1988 | Canada | 260/520.5 |
| 0145468 | 6/1985 | European Pat. Off. | 562/546 |

OTHER PUBLICATIONS

Lyons, J.E. "Selective Oxidation of Hydrocarbons" (1988) 245–258.
Lyons, J.E. et al. "Multiple Roles of Palladium in Liquid Phase Oxidation" (1986) 117–138.

*Primary Examiner*—Paul J. Killos
*Attorney, Agent, or Firm*—Richard J. Hicks

[57] ABSTRACT

A liquid phase process for the preparation of an (meth)-acrylate, such as methyl methacrylate, in the presence of water and a bi-functional, heterogeneous catalyst which contains both acidic and noble metal functional groups. The preferred (meth)-acrylate is methyl methacrylate (MMA). A surprising amount of MMA is produced, in spite of a competitive side reaction which produces methyl tertiary butyl ether (MTBE).

15 Claims, No Drawings

LIQUID PHASE PREPARATION OF (METH)-ACRYLATE FROM ALPHA-OLEFIN

This application is a continuation of application Ser. No. 08/238,401, filed May 5, 1994, now abandoned.

FIELD OF THE INVENTION

The invention relates to a liquid phase process for the preparation of (meth)-acrylates such as methyl methacrylate in the presence of a bi-functional, heterogeneous catalyst which contain both acidic and noble metal functionalities.

BACKGROUND OF INVENTION (Meth)-acrylates may be prepared by a well known process in which a carboxylic acid is esterified with an alcohol. For example, methyl methacrylate is produced by the reaction of methacrylic acid with methanol in the presence of an acidic catalyst. Thee methacrylic acid used in this reaction is typically pre-formed by the oxidation of isobutylene. A disadvantage of this conventional process is that it requires multiple reaction and purification operation. Prior researchers have attempted to mitigate the disadvantages of conventional processes by developing gas phase processes for the "single step" production of (meth)-acrylates. Notably, Miller et al (U.S. Pat. No. 4,060,545) disclose a process for the production of (meth)-acrylates by the oxidative esterification of propylene isobutylene in a single fluid bed reactor.

Other researchers developed metal oxide catalysts which are suitable for The single step, gas phase production of (meth)-acrylate. For example, Ferlazzo et al teach such catalysts in U.S. Pat. No. 3,925,463 and 4,014,925. The use of a catalyst containing phosphoric acid and palladium in a single step, gas phase process for producing (meth)-acrylates is taught by Murib et al in U.S. Pat. No. 3,758,551.

The above noted gas phase, single step, processes suffer from disadvantages common to all gas phase processes, namely that:

(a) large reactors are required in comparison to an analogous liquid phase process; and (b) energy efficiency suffers in gas phase processes (as a result of vapourization and condensation steps).

One liquid phase process for the production of (meth)-acrylates has been disclosed by Aoshima et al in U.S. Pat. No. 4,356,316.

It is an object of this invention to provide an improved liquid phase process for the production of (meth)-acrylate in the presence of a heterogeneous bi-functional catalyst. We have surprisingly discovered that a single heterogeneous catalyst having both acidic and noble metal functional groups will produce an (meth)-acrylate, in spite of the competing side reaction whereby the olefin is etherified with the alcohol.

SUMMARY OF THE INVENTION

By one aspect of this invention there is provided: a process for producing an (meth)-acrylate which comprises reacting, in the liquid phase, a $C_{3\ to\ 6}$ alpha-olefin with oxygen and a lower alcohol in the presence of water and a heterogeneous hi-functional catalyst having both of acidic functionality and catalytic metal functionality, wherein said catalytic metal is selected from the group consisting of the Group VIII metals of the Periodic Table.

The process of this invention employs a lower alcohol. As used herein, the term lower alcohol refers to an alcohol having from one to six carbon atoms and one —OH alcoholic functional group. The preferred alcohol is a primary alcohol such as methanol, ethanol, 1-propanol or 1-butanol, with methanol and ethanol being especially preferred.

The ratio of the $C_{3\ to\ 6}$ alpha olefin to the lower alcohol is not critical to the present process. A purpose of the lower alcohol is to esterify the carboxylic acid intermediate product which is produced by the oxidation of the alpha olefin. However, as all of the alpha olefin is typically not oxidized to the corresponding carboxylic acid, it is acceptable to use an excess molar ratio of alpha olefin to lower alcohol especially from about 3/1 to 7/1. In addition, the alcohol functions as a co-solvent to permit some miscibility of the substantially organic and substantially aqueous liquid phases in the system. The aforesaid amount of lower alcohol is sufficient to allow it to function as a co-solvent.

It is essential that water be present in the process of this invention. It is preferable that the water in the feed be in molar excess with respect to alpha olefin. It is especially preferred that the water/alpha olefin molar ratio in the feed be from 2/1 to 5/1.

The present invention incorporates an oxidation reaction which requires a source of oxygen. The oxygen source may either be pure oxygen or a dilute source of oxygen which contains a diluent such as nitrogen, helium, carbon dioxide of the like. Air may be employed as the oxygen source. The amount of oxygen present in the process of the present invention at any one time is not particularly critical. In fact, the oxygen concentration may be lower than the stoichiometric amount with respect to the alpha-olefin (although this will, obviously, slow down the rate of reaction) or it may be larger than the stoichiometric amount.

The process of the present invention uses a heterogeneous catalyst which contains a "noble" or Group VIII metal as a catalyst component. As used herein, the term "Group VIII metal" refers to a metal selected from the Group VIII metals of the Periodic Table of the Elements (as published, for example, in the 73rd edition of the CRC Handbook of Chemistry and Physics, edited by Little et al, published by the CRC Press, Boca Raton, 1992–1993, ISBN-0-8493-0473-3). Examples include platinum, palladium, rhodium and ruthenium, with palladium being highly preferred. The Group VIII metal is usually employed in the form of a solid. The amount of Group VIII metal used in the present process is not particularly critical to its success and may be readily optimized by persons skilled in the art using conventional procedures.

The catalyst metal must be supported. Common supports such as silica, alumina, carbon (charcoal) and the like are suitable. The catalyst must further include an acidic component. This is preferably accomplished by supporting the aforesaid Group VIE on an acidic support.

One example of an acidic support is a particulate ion exchange resin in $H^+$ form, such as a sulfonated divinyl benzene-styrene resin. This type of resin may be produced by well known techniques which generally involve the copolymerization of styrene and divinyl benzene to produce a particulate resin bead, followed by treatment of the resin bead with fuming sulfuric acid. It is especially preferred that the resin bead have a macroreticular structure. The resulting sulfonated styrene-divinyl benzene resin bead is a well known article of commerce and is sold, for example, by the Dow Chemical Company of Midland, Mich. under the registered trademark DOWLEX and by the Rohm and Haas company under the registered trademark AMBERLYST.

The above described sulfonated styrene-divinyl benzene resin beads are convenient for initial use and relatively inexpensive, but may be susceptible to deterioration during longer term use under commercial conditions. Accordingly, a more robust acidic support, such as a zeolite or an acid treated clay, may be preferable under higher temperature operating conditions. Palladium-loaded acidic zeolites are preferred examples of more robust heterogeneous catalysts for use in this invention. The preparation of Pd-loaded acidic zeolites is well known to those skilled in the art and is described, for example, in U.S. Pat. No. 4,992,617 (Schweizer et al). In general, acidic zeolites may be conveniently prepared by treating an alkaline zeolite with an aqueous acidic solution. Palladium (acetylacetonate)$_2$ is then used as a source of Pd for deposition on the acidic zeolite.

The operating temperature of the present process is up to 150° C., with temperatures between 40° and 80° C. being particularly preferred. The operating pressure is such that the alpha olefin is substantially liquid at the operating temperature. By way of a non-limiting, specific example, an operating temperature of 60°-75° C. and an operating pressure of 10-15 atmospheres is suitable when the alpha olefin is isobutylene.

One particular advantage of the present invention is that the liquid phase operating conditions reduce the required reactor size which, in turn, lowers capital investment requirements. In addition, the inventive process is energy efficient in that the (meth)-acrylate product is not vapourized and/or condensed.

One disadvantage of a liquid phase oxidation of a $C_{3\ to\ 6}$ alpha olefin is that an intermediate product (a carboxylic acid) has a tendency to polymerize and thereby cause a reduction in product yield. The process of the present invention mitigates this problem through the use of added water. As noted above, the molar amount of water is preferably between 2/1 and 5/1 with respect to the alpha olefin.

This polymerization problem is further mitigated by:

(1) the required use of the lower alcohol (because, as previously noted, the alcohol reacts with the carboxylic acid to produce the desired (meth)-acrylate product); and (2) the preferred, but optional, use of at least one polymerization inhibitor.

Suitable polymerization inhibitors are well known to those skilled in the art and include quinones, butylated hydroxy toluene (BHT) and methoxy phenol.

During the course of our experimental activity, we have typically observed the presence of more than one liquid phase. It is believed that one liquid phase is substantially hydrocarbon (or "organic"), and that the second liquid phase is aqueous. We have further determined that it is highly preferable to utilize a polymerization inhibitor in the aqueous feed stream (especially hydroquinone, at a concentration of from 1000 to 2000 ppm) and at least one polymerization inhibitor in the organic feed stream (especially a combination of methoxy phenol and quinone, each at a concentration of from 1000 to 2000 ppm).

The above described conditions—namely the presence of more than one liquid phase and the use of more than one polymerization inhibitor—are features of a highly preferred embodiment of the process of this invention.

Other preferred embodiments of this invention include the use of MTBE as a feedstock for the production of methyl methacrylate and the operation of the present process under conditions such that one or more components of the substantially organic phase is at or near its boiling point, as explained below.

The use of MTBE as a feedstock for the preparation of methyl methacrylate is preferred for reasons of cost and market demand. That is, the market demand for methyl methacrylate is such that it is presently considered to be the (meth)-acrylate of most commercial interest to us. The preparation of methyl methacrylate may use isobutylene and methanol as feedstocks. Methyl-tertiary butyl ether (or MTBE) is now a widely available and inexpensive item of commerce. It is known that isobutylene and methanol may be obtained by "back-cracking" MTBE (for example, by subjecting MTBE to heat, in the presence of an acidic catalyst). Thus, for reasons of cost, it is preferred to obtain isobutylene and methanol for use in the present invention by the back-cracking of MTBE.

In a highly preferred embodiment of this invention, the process is operated under pressure and temperature conditions such that:

(a) a substantially organic phase and a substantially aqueous phase exist; and (b) at least one liquid component is at or near its boiling point.

These highly preferred operating conditions help to reduce/eliminate severe temperature gradients, as the enthalpy of evaporation serves to moderate temperature fluctuations.

Further details of the invention are illustrated by the following non-limiting examples.

EXAMPLE 1

Oxidation of Isobutylene (Comparative)

This example is comparative in that a linear alcohol is not used. Accordingly, the tendency towards polymerization of the intermediate carboxylic acid (in this case, methacrylic acid) is severe. This example illustrates that the formation of polymer can be reduced through the use of more than one polymerization inhibitor.

Experimental details are set out below.

Apparatus

The reactor consisted of a length of 1.5" (3.8 cm) inside diameter stainless steel pipe which included two 6.0 inch (15 cm) heated zones. The interior surfaces of the pipe were polished to remove surface defects. Liquid feed streams and inhibitor flows were introduced via positive displacement pumps. Gases were metered by differential pressure measurements. The aqueous, organic and vapour streams were introduced into the bottom of the reactor and were allowed to flow upwardly through a six inch length (15 cm) preheater zone which was filled with ceramic beryl saddles. The reaction mixture left the preheater zone and passed through a two inch (5 cm) length zone of wire gauze to ensure good distribution/mixing of the phases.

The six inch (15 cm) length reaction zone was packed with catalyst and ceramic saddles. Liquid product exited the reactor via a liquid drain line and vapour exited to a condenser. Cooling water for the condenser was supplied by a refrigeration unit at a temperature of 4° C. Liquid from the reactor was combined with condensate and directed to a phase separator where the organic/aqueous phases were separated. The organic phase from the separator flowed to a collection pot to enable continuous monitoring of weight gain. The aqueous products were periodically drained from the phase separator and measured by volume. The gaseous stream which exited the condenser was directed through a pneumatic backpressure control valve which regulated the overall system pressure. Exiting gas flow rates were measured by displacement of water from a calibrated burette.

Reactor temperature was measured by one thermocouple located at the exit of the preheater and a second thermocouple located near the middle of the reaction zone. The length of the reactor was surrounded by exterior heating elements and controlled via PID controllers.

The reactor was loaded with 20 grams of catalyst. The catalyst was palladium (0) supported on carbon (5 weight % Pd(0) on carbon).

Analysis of the product was carried out by gas chromatography (GC). A Gas Chromatograph/Mass Spectrometer (tradename: Varian Saturn II GC/MS) was used to confirm product identification and selectivity data.

The reaction zone was purged of oxygen with nitrogen then treated for 18 hours whilst submerged in water by passing isobutylene over the bed at a rate of 1.5 g/minute at a temperature of about 70° C. and a pressure of about 138 psig (about 950 kPa). As a control, a blank run (i.e. no catalyst) was completed to confirm that product was not detected in the absence of catalyst.

Feed and inhibitor were then introduced into the reactor in the amounts set out below:

| Feed | |
|---|---|
| isobutylene | 152 g/hr |
| water | 198 g/hr |
| oxygen | 70.3 l/hr |
| nitrogen | 263 l/hr |
| Inhibitors | |
| Aqueous | hydroquinone: 1000 ppm |
| Organic 1 | Methoxy Phenol: 1000 ppm |
| Organic 2 | Quinone: 1000 ppm |

Analysis of the output streams provided an estimated isobutylene conversion of between 8 and 12 weight % with a product selectivity of 76 weight methacrylic acid and 24 weight % methacrolein.

The run was conducted over an 8 hour period without detectable levels of polymer formation. Surprisingly, there was no evidence of carbon dioxide or carbon monoxide formation.

In a series of similar experiments conducted without the polymerization inhibitors, the reactor system was quickly rendered inoperative as a result of polymer formation.

EXAMPLE 2

This example illustrates the single step, liquid phase production of methyl methacrylate using a heterogenous catalyst containing both acidic functionality and palladium.

The heterogeneous catalyst was a palladium loaded, sulfonated styrene-divinyl benzene resin. Thus, the catalyst contains both of a heterogeneous acidic functionality (in the form of the resin bound $H^+SO_3^-$ groups) and Pd. The Pd loading was reported by the catalyst supplier to be 5% (weight basis), and the catalyst was sold under the trademark Lewatit OC 1038 by Bayer AG of Leverkusen, Germany.

A laboratory scale batch reactor was used for the experiment of this example.

The feed consisted of 0.56 gram moles of water (containing 1500 ppm hydroquinone inhibitor); 0.123 gram moles of methanol and 0.536 gram moles of isobutylene. Oxygen was fed into the reactor to a pressure of 200 psi gauge ($1.38 \times 10^4$ kilo Pascals gauge) at 20° C. The reactor was then agitated for two hours at 70° C. An organic layer and an aqueous layer were observed upon opening the reactor. Analysis of the organic layer by gas chromatography provided an estimate of the relative amounts of material in the organic phase as being: isobutylene 50 weight %, methyl-tertiary butyl ether (MTBE) 10% and methyl methacrylate 40%. The presence of the MTBE is not unexpected, as it is well known that heterogeneous —$SO_3^-H^+$ groups will catalyze the etherification of isobutylene with methanol at the operating temperature of this example.

It is, however, surprising that a substantial amount of methyl methacrylate is produced on this bi-functional catalyst—in spite of the competing reaction to produce MTBE.

The embodiments of the invention in which an exclusive property or privilege is claimed are defined as follows:

1. A process for producing an (meth)-acrylate which comprises reacting, in the liquid phase, a $C_{3 \text{ to } 6}$ alpha-olefin with oxygen and a lower alcohol in the presence of (a) water and (b) a heterogeneous bi-functional catalyst having both of acidic functionality and catalytic metal functionality, wherein said metallic catalyst consists essentially of a metal selected from the Group VIII metals of the Periodic Table.

2. A process as claimed in claim 1 wherein said lower alcohol contains one —OH alcoholic functional group and from 1–6 carbon atoms.

3. A process as claimed in claim 2 wherein said alcohol is selected from the group consisting of methanol, ethanol, 1-propanol and 1-butanol.

4. The process of claim 1 which is further characterized by the presence of more than one liquid phase during said catalytic reaction.

5. The process of claim 1 when undertaken in the presence of an additive which is an (meth)-acrylate polymerization inhibitor.

6. The process of claim 1 wherein said heterogeneous bi-functional catalyst consists of a Pd-loaded acidic zeolite.

7. The process of claim 1 wherein said bi-functional catalyst consists of a particulate, acidic cationic exchange resin having deposited thereon said catalytic metal.

8. The process of claim 7 wherein said catalytic metal is palladium.

9. The process of claim 8 wherein said particulate, acidic cationic exchange resin is the reaction product of a crosslinked divinyl benzene-styrene resin with sulfuric acid.

10. The process of claim 1 wherein said alpha-olefin is isobutylene, said alcohol is methanol and said (meth)-acrylate is methyl methacrylate.

11. The process of claim 10 wherein said isobutylene and methanol are obtained by the back-cracking of methyl tertiary butyl ether.

12. The process of claim 4 wherein said more than one liquid phase includes a substantially organic liquid phase and a substantially aqueous liquid phase.

13. The process of claim 12 when operated at or near the boiling point of at least one liquid organic contained therein.

14. The process of claim 11 when undertaken at a pressure of from 10–15 atmospheres and a temperature of from 40° C. to 80° C.

15. The process of claim 14 wherein said temperature is in the range of 60°–75° C.

* * * * *